(12) United States Patent
Taguchi et al.

(10) Patent No.: US 8,920,467 B2
(45) Date of Patent: Dec. 30, 2014

(54) LOW BACK PAIN TREATMENT TOOL

(76) Inventors: Hiroshi Taguchi, Tokyo (JP); Akiko Taguchi, Tokyo (JP)

( * ) Notice: Subject to any disclaimer, the term of this patent is extended or adjusted under 35 U.S.C. 154(b) by 620 days.

(21) Appl. No.: 13/375,329

(22) PCT Filed: Apr. 21, 2011

(86) PCT No.: PCT/JP2011/059839
§ 371 (c)(1),
(2), (4) Date: Nov. 30, 2011

(87) PCT Pub. No.: WO2012/124175
PCT Pub. Date: Sep. 20, 2012

(65) Prior Publication Data
US 2013/0030464 A1   Jan. 31, 2013

(30) Foreign Application Priority Data

Mar. 14, 2011 (JP) ................................. 2011-076520

(51) Int. Cl.
*A61H 1/00* (2006.01)
*A61F 5/01* (2006.01)

(52) U.S. Cl.
CPC *A61F 5/01* (2013.01); *A61H 1/006* (2013.01); *A61H 2201/1284* (2013.01); *A61H 2201/1623* (2013.01); *A61H 2201/1635* (2013.01); *A61H 2201/1664* (2013.01); *A61H 2203/0431* (2013.01); *A61H 2205/081* (2013.01)
USPC ............ 606/237; 606/238; 606/240; 128/845

(58) Field of Classification Search
USPC ........... 601/23, 24, 84, 86, 90, 91, 92, 95, 97, 601/98, 107; 606/201, 204, 237, 238, 606/240–245; 128/845, 846; 5/621, 624, 5/630, 652, 648; 602/32
See application file for complete search history.

(56) References Cited

U.S. PATENT DOCUMENTS

| 2,818,854 | A  | * | 1/1958  | Johnson .......................... 606/240 |
| 5,626,616 | A  | * | 5/1997  | Speece ........................... 606/240 |
| 6,125,851 | A  | * | 10/2000 | Walker et al. ................... 128/845 |
| 6,311,349 | B1 | * | 11/2001 | Kazakia et al. ................. 128/845 |
| 7,060,085 | B2 | * | 6/2006  | Graham et al. ................. 606/240 |
| 2003/0130696 | A1 | * | 7/2003  | Hurd .............................. 606/240 |

FOREIGN PATENT DOCUMENTS

| JP | 8-126718    | 5/1996 |
| JP | 2010-188171 | 9/2010 |

* cited by examiner

*Primary Examiner* — Quang D Thanh
(74) *Attorney, Agent, or Firm* — Hamre, Schumann, Mueller & Larson, P.C.

(57) ABSTRACT

The invention provides a lumbago treatment instrument which manipulates the pelvis safely and properly by pressing the coccyx utilizing the patient's own body weight. A coccyx contact treatment member is disposed inside a cylindrical casing so as to be movable in the vertical direction via an elastic member. A coccyx contact buffering member made of sponge or the like is provided on the upper end of the coccyx contact treatment member. The patient straddles the coccyx contacting buffering member, assuming a sitting posture, and places the coccyx on the coccyx contact buffering member. In this posture, both feet are slightly lifted from the floor to apply the body weight on the coccyx contact buffering member so that the coccyx is pushed up from below. When doing so, the patient continues to maintain an upright posture while pressing the upper body against a posture holding member and gripping a handle with both hands.

4 Claims, 7 Drawing Sheets

LOW BACK PAIN TREATMENT TOOL

TECHNICAL FIELD

The present invention relates to a low back pain treatment tool by means of correction of the sacrum, ilium, coccyx, or the like, or more specifically, by means of correction of the pelvis constituted thereby.

BACKGROUND ART

Pelvis correction is the most common method of relieving low back pain.

As a conventional method for pelvis correction, there has been available a treatment method which uses a belt or traction device for fastening the pelvis. A temporary effect can be obtained by compressing only the pelvis using such a device, but the effect does not last very long: for example, the pain comes back after a predetermined period of time elapses since the end of the use of the belt or the like.

Examples of such a device include the one that uses a geared motor (Patent Document 1) and the one that requires a recipient to perform light exercise (Patent Document 2). These devices should be used on a recipient who is in a sitting position, a supine position, or the like, and are not designed for correcting the pelvis while he/she raises his/her body up, or more specifically, is in a "standing position" which is a stable state for the lumbar vertebra. In addition, the use of a mechanical device such as a motor may lead to excessive correction depending on how it is used.

PRIOR ART DOCUMENT

Patent Document

Patent Document 1: Japanese Unexamined Patent Application Publication No. 2010-188171
Patent Document 2: Japanese Unexamined Patent Application Publication No. 8-126718

SUMMARY OF THE INVENTION

Problems to be Solved by the Invention

The followings are the problems to be solved.
1. Only a temporary effect can be obtained by compressing the pelvis.
2. The pelvis is not corrected while a recipient is in a "standing position" which is a stable state for the lumbar vertebra.
3. A device which uses a motor may provide excessive correction.
4. A device which requires light exercise lacks in convenience, and limits users who can use it.

In consideration of the above problems, it is an object of the present invention to provide a low back pain treatment tool which can correct the pelvis while a recipient is in a "standing position," and which safely and properly corrects the pelvis by pressing the coccyx using the weight of the recipient.

Means for Solving the Problem

As described in claim 1, the present invention is a low back pain treatment tool comprising: a cylindrical casing elongated in a longitudinal direction; a coccyx contact treatment member which is slidably placed through an elastic member in an axial direction of the cylindrical casing; a coccyx contact buffering member which is provided on an upper end of the coccyx contact treatment member; a posture holding member having a posture holding surface in a longitudinal direction, which faces the cylindrical casing; and a handle fixed to the posture holding member.

In addition, as described in claim 2, the present invention is the low back pain treatment tool according to claim 1, wherein the cylindrical casing is fixed and supported on the posture holding member by fixing a horizontal seat plate vertically with respect to the posture holding surface and coupling a lower end of the cylindrical casing to an upper surface of the horizontal seat plate.

Further, as described in claim 3, the present invention is the low back pain treatment tool according to claim 1, wherein the cylindrical casing is fixed and supported on the posture holding member by fixing the posture holding member on a horizontal base plate, fixing a pair of left and right side plates orthogonally to a horizontal surface of the base plate and the posture holding surface, and attaching a horizontal seat plate between the side plates.

Still further, as described in claim 4, the present invention is a low back pain treatment tool comprising: a cylindrical casing elongated in a longitudinal direction; a coccyx contact treatment member which is slidably placed through an elastic member in an axial direction of the cylindrical casing; a coccyx contact buffering member which is provided on an upper end of the coccyx contact treatment member; a posture holding member having a posture holding surface in a longitudinal direction, which faces the cylindrical casing; a handle fixed to the posture holding member; a horizontal seat plate which fixes and supports the cylindrical casing on the posture holding member by being fixed vertically with respect to the posture holding surface and coupling a lower end of the cylindrical casing to an upper surface of the horizontal seat plate; a horizontal base plate which fixes the posture holding member; a pair of left and right side plates which are fixed orthogonally to a horizontal surface of the base plate and the posture holding surface, and which support left and right sides of the horizontal base plate respectively; corner portions formed by an outer surface of either of the side plates, the posture holding surface, and a horizontal surface of the base plate; and rectangular parallelepiped foot rest blocks which are detachably placed at the corner portions.

Effects of the Invention

According to the invention set forth in claim 1, riding on the coccyx contact treatment member of the low back pain treatment tool in a "standing position" can restore the downward movement of the spine by upward vertical compression from immediately below the coccyx using the "weight of the recipient".

Treating a recipient in a "standing position" can allow positional correction of the sacrum, ilium, coccyx, or the like, or more specifically, correction of the pelvis constituted thereby, in a stable state for the lumbar vertebra, making it possible to continuously relieve low back pain.

By vertically vibrating the coccyx contact treatment member which is slidably placed through the elastic member, while riding on it, a recipient can finely adjust the position of the coccyx contact treatment member at the pelvis, so that he/she can achieve pelvis correction at a proper position.

According to the invention set forth in claim 2, the cylinder casing is fixed and supported on the posture holding member by fixing the cylinder casing on the upper surface of the horizontal seat plate provided at a proper height, the length of the cylinder casing can be reduced. This prevents excessive moment force from being applied to the bolt which is located at the basal portion of the cylinder casing to fix it, thereby reducing the occurrence of failures. In addition, shorter length of the cylinder casing can save on costs.

According to the invention set forth in claim 3, by providing the pair of left and right side surface plates fixed orthogonally to the horizontal seat plate and the posture holding surface of the posture holding member, the orientation of the horizontal seat plate can be kept constant even under load of the weight of the recipient.

According to the invention set forth in claim 4, the rectangular parallelepiped foot rest blocks are stably provided in place at the corner portions, which are formed by three surfaces consisting of the outer surface of either of the side plates, the horizontal surface of the base plate, and the posture holding surface, so that the blocks can simultaneously come into contact with the surfaces. Thereby the recipient can more easily apply his/her weight to the coccyx contact treatment member in a "standing position" while riding on the treatment tool. More specifically, he/she can thereby appropriately select and easily adjust the height at which he/she can take his/her feet off the foot rest blocks while riding on the treatment tool, and can also make height adjustment in accordance with his/her height, before he/she uses the treatment tool.

Figure 1:
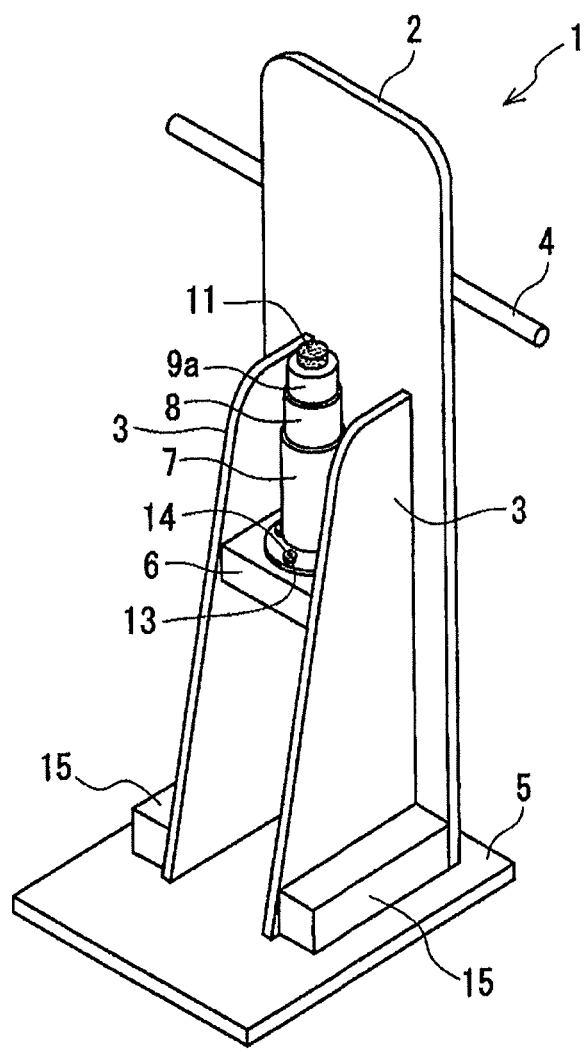
FIG. 1 is an overall view of a low back pain treatment tool according to Embodiment 1 of the present invention.

BEST MODES FOR CARRYING OUT THE INVENTION (Embodiment 1)

Embodiment 1 of the present invention will be described below with reference to FIGS. 1 and 2.

With a cylindrical casing 7 placed so that its axial direction is along the vertical direction, an inner cylindrical casing 8 and a coccyx contact treatment member 9a, each having a smaller diameter than that of the casing 7, are inserted thereinto. In this case, a coil spring as an elastic member 10 is provided below the inner cylindrical casing 8, and then the inner cylindrical casing 8 and the coccyx contact treatment member 9a are arranged so that they can slide vertically relative to the casing 7. With such an arrangement, the coccyx contact treatment member 9a is placed so that it can slide in the axial direction of the casing 7 through the elastic member 10.

The coccyx contact treatment member 9a has a cylindrical shape, is configured so that its diameter can be changed in accordance with the body size of a recipient, and has a flat surface to be contacted by the recipient. It should be noted, however, that a coccyx contact treatment member 9b having projections on the surface to be contacted by the recipient, may be used depending on the symptoms of low back pain of the recipient.

A sponge is provided as a coccyx contact buffering member 11 in a center of a recipient-side end face of the coccyx contact treatment member 9a or 9b to avoid excessive compression of the coccyx of the recipient.

A base for supporting the cylindrical casing 7 is constituted by a horizontal seat plate 6, a pair of side plates 3 provided on the left and right sides of the horizontal seat plate 6, and a base plate 5. The cylindrical casing 7 is fixed to the horizontal seat plate 6, which is a constitute element of the base, with bolts 12, washers 13, and nuts 14.

A posture holding member 2 which is used by a recipient to hold his/her posture when he/she rides on the coccyx contact treatment member 9a has a posture holding surface of a plate-like shape elongated in the vertical direction, and is provided adjacent to the cylindrical casing 7 to be fixed to the base plate 5, side plates 3, and horizontal seat plate 6.

A handle which is used by a recipient when he/she rides on the coccyx contact buffering member 11 is fixed to the posture holding member 2. Rectangular parallelepiped foot rest blocks 15 for a recipient are placed at corner portions formed by three surfaces consisting of the outer surface of either of the side plates 3, the posture holding surface of the posture holding member 2, and the horizontal surface of the base plate, so that the blocks can simultaneously come into contact with the surfaces.

Figure 5:
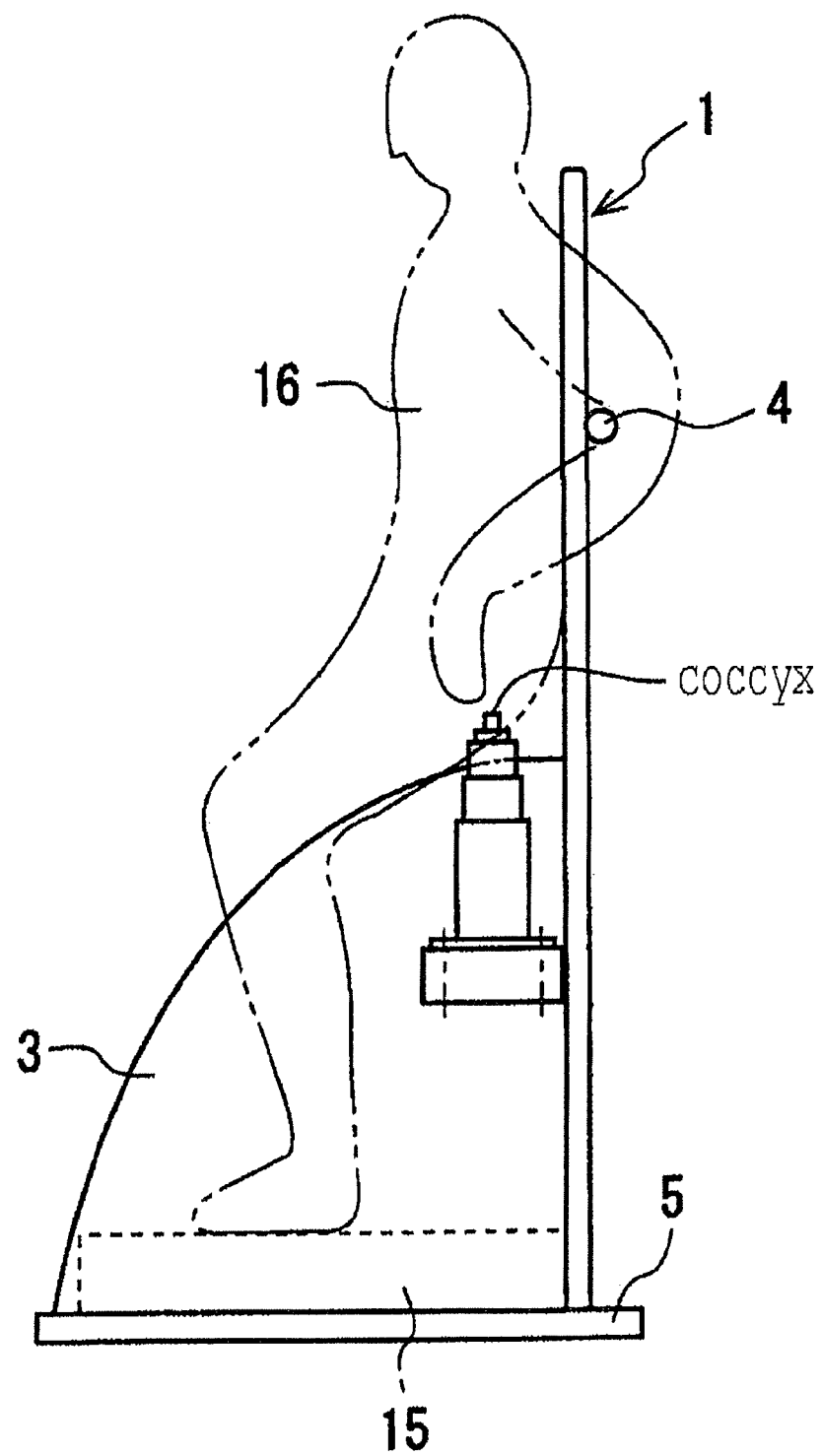
FIG. 5 is a schematic view showing a case where a wood hand/arm holding portion shown in Embodiment 1 of the present invention is used on the back of a recipient.

A method of using a low back pain treatment tool 1 according to the above-mentioned embodiment will be described with reference to FIG. 5. FIG. 5 is a view showing a case where a hand/arm holding portion 4 as a handle is used so that the back of a recipient comes into contact with the posture holding member 2. The recipient straddles the cylindrical casing 7 of the low back pain treatment tool 1 to place his/her coccyx on the coccyx contact buffering member 11. At this time, the recipient spreads his/her legs by about the breadth of his/her shoulders in a standing position. With his/her back against the posture holding member 2, the recipient then stretches his/her arms backward over the hand/arm holding portion 4 as a handle, bends his/her arms so that the handle is located on the inside of his/her elbows, and takes his/her forearms toward the front of him/her from below the handle. Thereby, the recipient can stably keep himself/herself in a standing position. Depending on the symptoms of his/her low back pain, he/she may correct his/her pelvis and relieve his/her pain by using the low back pain treatment tool 1 for five minutes per use and about two times per day.

The foot rest blocks 15 have a rectangular parallelepiped shape, and hence can be easily positioned at the corner portions formed by the three surfaces consisting of the outer surface of either of the side plates 3, the posture holding surface of the posture holding member 2, and the horizontal surface of the base plate 5, while simultaneously coming into contact with the three surfaces. Thereby the recipient can more easily apply his/her weight to the coccyx contact treatment member 11 in a "standing position" while riding on the treatment tool. More specifically, he/she can thereby appropriately select and easily adjust the height at which he/she can take his/her feet off the foot rest blocks while riding on the treatment tool, and can also make height adjustment in accordance with his/her height by stacking two or more foot rest blocks 15 or replacing the foot rest blocks 15 with ones of different heights, before he/she uses the treatment tool.

Figure 6:
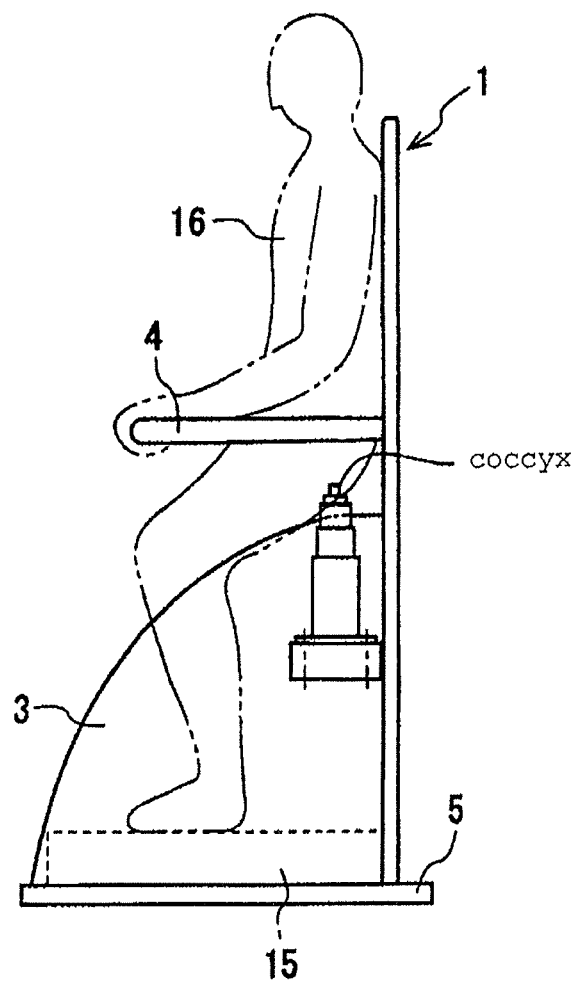
FIG. 6 is a schematic view showing a case where the wood hand/arm holding portion shown in Embodiment 1 of the present invention is used as an armrest.
Figure 7:
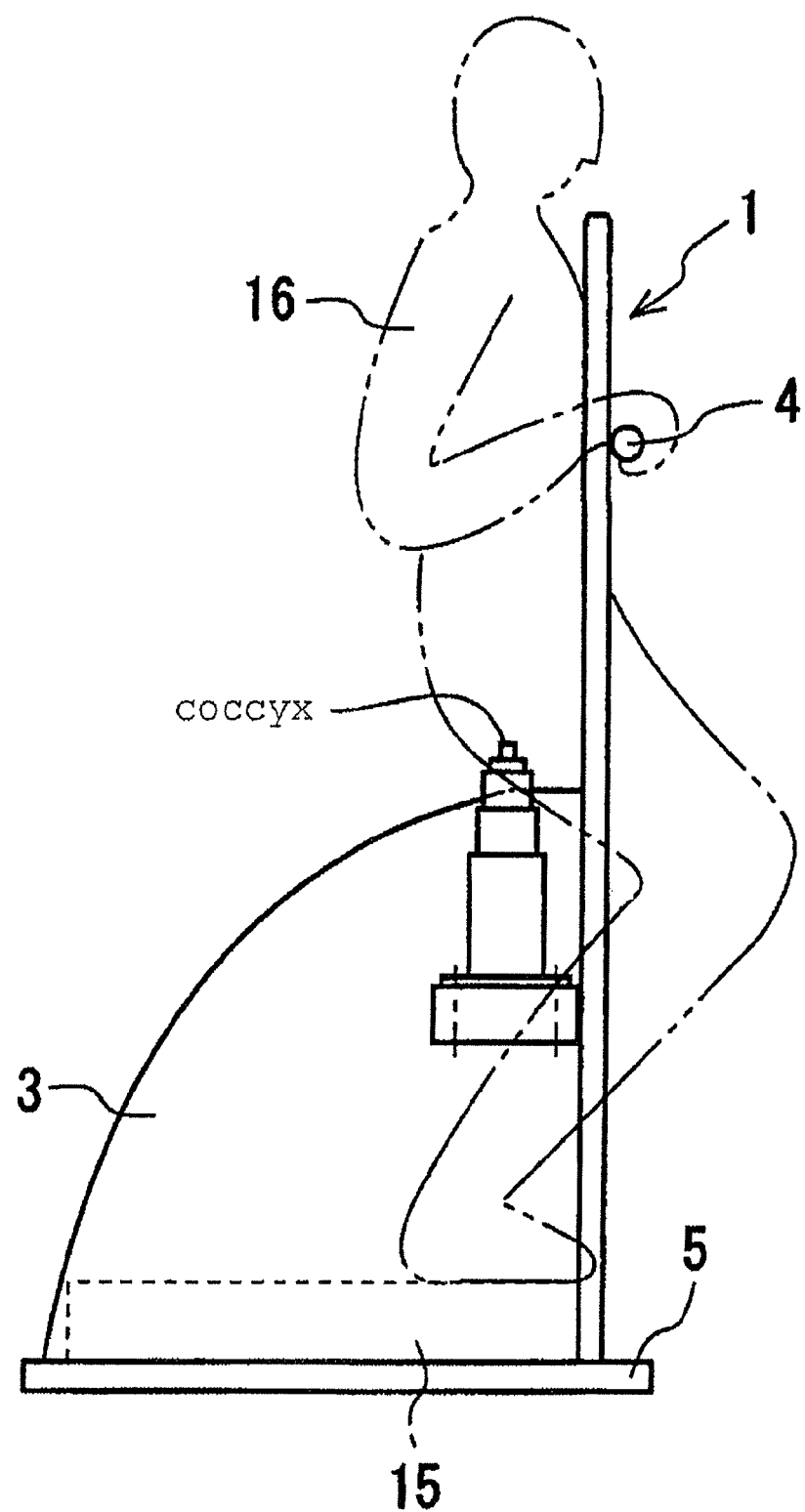
FIG. 7 is a schematic view for explaining a case where the wood hand/arm holding portion shown in Embodiment 1 of the present invention is used in front of the recipient, with his/her chest and abdomen pressed against a posture holding surface.

The coccyx contact treatment member 9a is slidably placed through the elastic member, and therefore, when the recipient places his/her coccyx on the coccyx contact buffering member 11, he/she finely adjusts the position of the coccyx contact treatment member 9a by vertically vibrating the coccyx contact treatment member 9a while riding on it. FIG. 6 is a view showing a case where the low back pain treatment tool according to the present invention is used with hand/arm holding portions 4 as handles being used as armrests. FIG. 7 is a view showing a case where the low back pain treatment tool according to the present invention is used with the chest and abdomen of a recipient pressed against the posture holding member 2.

(Embodiment 2)

Embodiment 2 of the present invention will be described with reference to FIG. 3.

The internal configuration of a cylindrical casing 7 is the same as that in Embodiment 1.

In this embodiment, the cylindrical casing 7 is directly fixed to a base plate 5, which is a constituent element of a base, with bolts 12, washers 13, and nuts 14.

Longer longitudinal length of the cylindrical casing 7 reduces the number of components and allows simpler configuration as compared with Embodiment 1.

(Embodiment 3)

Figure 4:
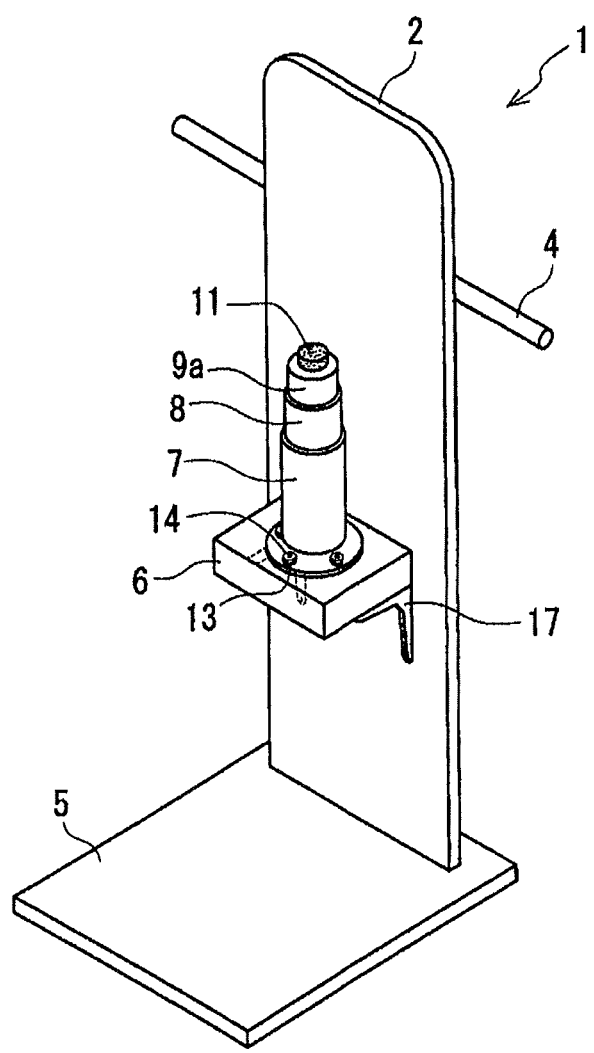
FIG. 4 is an overall view of a low back pain treatment tool according to Embodiment 3 of the present invention.

Embodiment 3 of the present invention will be described with reference to FIG. 4.

The internal configuration of a cylindrical casing 7 is the same as that in Embodiment 1.

In this embodiment, a base for supporting a cylindrical casing 7 is constituted by a horizontal seat plate 6 and a base plate 5. The cylindrical casing 7 is fixed to the horizontal seat plate 6, which is a constitute element of the base, with bolts 12, washers 13, and nuts 14. The horizontal seat plate 6 is fixed to a posture holding member 2 with shelf supports 17, and the posture holding member 2 is fixed to the base plate 5 with bolts.

In this embodiment, it is only required to fix the horizontal seat plate 6 to the posture holding member 2, and therefore, as in the second embodiment, the number of components is smaller and simpler configuration is possible than in Embodiment 1.

The upper end faces of the cylindrical casing 7 and the coccyx contact treatment member 9a are circular so as not to injure a recipient in FIG. 1, but are not limited to this, and may be elliptic for example. Further, in FIG. 1, the coccyx contact treatment member 9a is separated from an inner cylindrical casing 8 in consideration of the possibility that a recipient may change the shape of the coccyx contact treatment member 9a. However, no problem arises even if these components are integrated Again in FIG. 1, the coccyx contact treatment member 9a is smaller in diameter than the cylindrical casing 7, so that the coccyx contact treatment member 9a is placed inside the cylindrical casing 7. However, the present invention is not limited to this configuration, and the coccyx contact treatment member 9a may cover the cylindrical casing 7.

Figure 2:
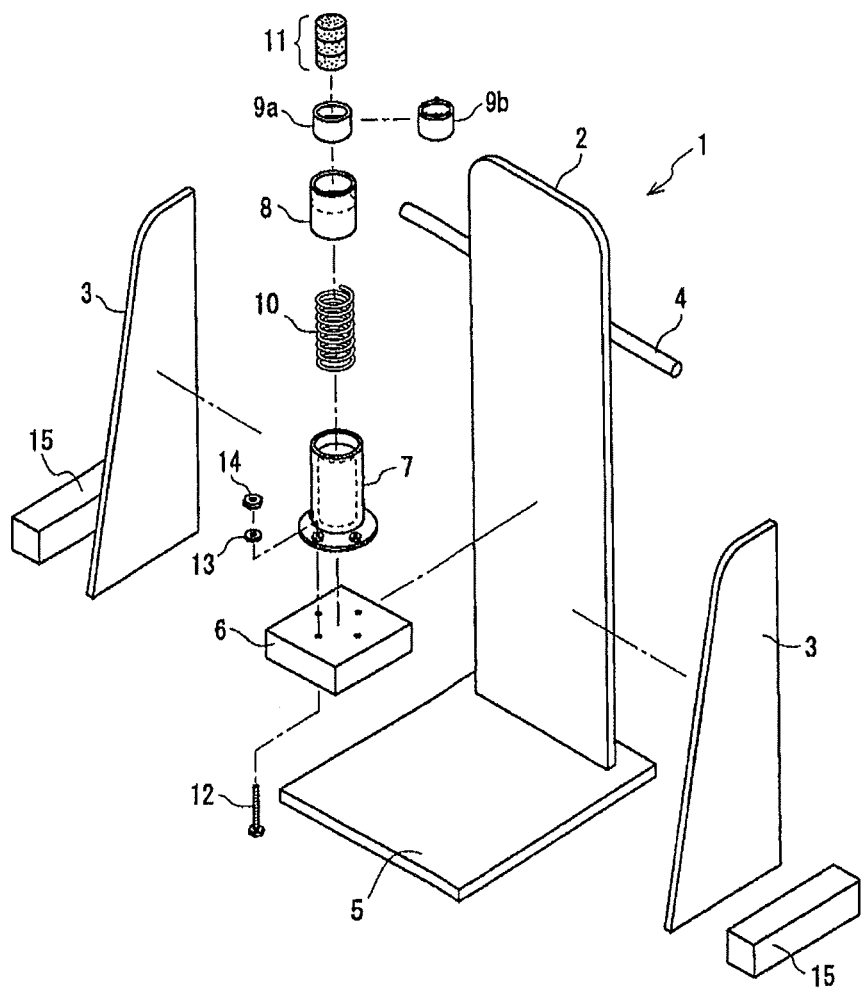
FIG. 2 is a developed view of the low back pain treatment tool according to Embodiment 1 of the present invention.

The elastic member 10 can be changed in accordance with the weight or symptoms of the recipient, and a coil spring is used in FIG. 2, but a leaf spring or rubber may be used as the elastic member 10.

The coccyx contact treatment member 9a or 9b comes into contact with a recipient, and hence is preferably made of wood. However, depending on the symptoms of the recipient, the coccyx contact treatment member 9a or 9b may be made of rubber which is softer than wood, or aluminum which is harder than wood.

The horizontal seat plate 6 and the cylindrical casing 7 are fixed with bolts in FIG. 2. However, the present invention is not limited to this, and they may be fixed, for example, with a wedge or by fitting.

The hand/arm holding portion 4 which is used as a handle in FIGS. 5 and 6 is rodlike. However, the shape of the hand/arm holding portion 4 is not limited to this, and may be platelike.

Figure 3:
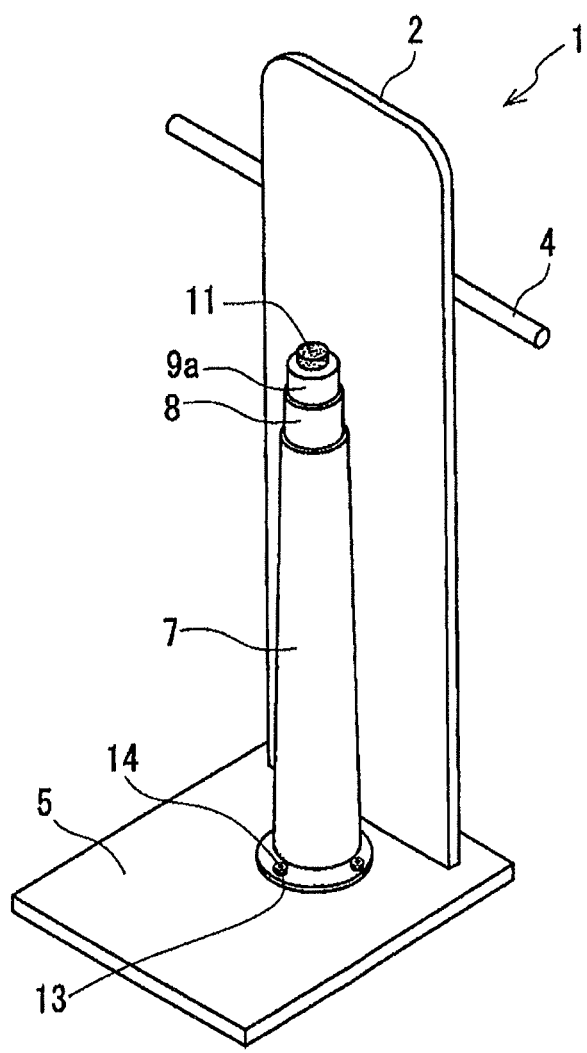
FIG. 3 is an overall view of a low back pain treatment tool according to Embodiment 2 of the present invention.

Referring to FIG. 3, the hand/arm holding portion 4 is coupled to the posture holding member 2 so as to allow height adjustment.

DESCRIPTION OF REFERENCE NUMERALS

1: Low back pain treatment tool
2: Posture holding plate
3: Side plate
4: Hand/arm holding portion
5: Base plate
6: Horizontal seat plate
7: Cylindrical casing
8: Inner cylindrical casing
9a: Coccyx contact treatment member
9b: Coccyx contact treatment member having projections
10: Elastic member
11: Coccyx contact buffering member
12: Casing fixing bolt
13: Casing fixing washer
14: Casing fixing nut
15: Foot rest block
16: Human body
17: Shelf support

The invention claimed is:

1. A low back pain treatment tool comprising:
a cylindrical casing elongated in a longitudinal direction;
a coccyx contact treatment member which is placed through an elastic member so as to be slidably movable in an axial direction of the cylindrical casing;
a coccyx contact buffering member which is provided on an upper end of the coccyx contact treatment member;
a posture holding member which has a posture holding surface in a longitudinal direction, which faces the cylindrical casing; and
a handle fixed to which the posture holding member.

2. The low back pain treatment tool according to claim 1, wherein the cylindrical casing is fixed and supported on the posture holding member by fixing a horizontal seat plate vertically with respect to the posture holding surface and coupling a lower end of the cylindrical casing to an upper surface of the horizontal seat plate.

3. The low back pain treatment tool according to claim 1, wherein the cylindrical casing is fixed and supported on the posture holding member by fixing the posture holding member on a horizontal base plate, fixing a pair of left and right side plates orthogonally to a horizontal surface of the base plate and the posture holding surface, and attaching a horizontal seat plate between the side plates.

4. A low back pain treatment tool comprising:
a cylindrical casing elongated in a longitudinal direction;
a coccyx contact treatment member which is slidably placed through an elastic member in an axial direction of the cylindrical casing;
a coccyx contact buffering member which is provided on an upper end of the coccyx contact treatment member;
a posture holding member having a posture holding surface in a longitudinal direction, which faces the cylindrical casing;

a handle fixed to the posture holding member;

a horizontal seat plate which fixes and supports the cylindrical casing on the posture holding member by being fixed vertically with respect to the posture holding surface and coupling a lower end of the cylindrical casing to an upper surface of the horizontal seat plate;

a horizontal base plate which fixes the posture holding member;

a pair of left and right side plates which are fixed orthogonally to a horizontal surface of the base plate and the posture holding surface, and which support left and right sides of the horizontal base plate respectively;

corner portions formed by an outer surface of either of the side plates, the posture holding surface, and a horizontal surface of the base plate; and rectangular parallelepiped foot rest blocks which are detachably placed at the corner portions.

\* \* \* \* \*